US011673025B2

(12) United States Patent
Rauhala et al.

(10) Patent No.: US 11,673,025 B2
(45) Date of Patent: Jun. 13, 2023

(54) WORKOUT RECOMMENDATION ENGINE

(71) Applicant: PEAR Sports LLC, Newport Beach, CA (US)

(72) Inventors: Kari Kristian Rauhala, Solana Beach, CA (US); Eric Franchomme, San Diego, CA (US); Micah Kendrick Peng, San Diego, CA (US); Sam Daniel Arvidsson, San Diego, CA (US); Anton Dembowski, Los Angeles, CA (US); Gregory John Altin, San Diego, CA (US)

(73) Assignee: PEAR Sports LLC, Newport Beach, CA (US)

( * ) Notice: Subject to any disclaimer, the term of this patent is extended or adjusted under 35 U.S.C. 154(b) by 729 days.

(21) Appl. No.: 16/459,564

(22) Filed: Jul. 1, 2019

(65) Prior Publication Data

US 2020/0001134 A1  Jan. 2, 2020

Related U.S. Application Data

(60) Provisional application No. 62/692,521, filed on Jun. 29, 2018.

(51) Int. Cl.
| | | |
|---|---|---|
| *G06F 3/048* | (2013.01) | |
| *A63B 24/00* | (2006.01) | |
| *G06F 3/01* | (2006.01) | |
| *G16H 20/60* | (2018.01) | |
| *G16H 20/30* | (2018.01) | |
| *A61B 5/00* | (2006.01) | |

(52) U.S. Cl.
CPC ........ *A63B 24/0075* (2013.01); *A61B 5/6804* (2013.01); *A63B 24/0062* (2013.01); *G06F 3/011* (2013.01); *G16H 20/30* (2018.01); *G16H 20/60* (2018.01); *A63B 2024/0081* (2013.01)

(58) Field of Classification Search
CPC ............ A63B 24/0075; A63B 24/0062; A63B 2024/0081; G16H 20/30; G16H 20/60; A61B 5/6804; G06F 3/011
See application file for complete search history.

(56) References Cited

U.S. PATENT DOCUMENTS

| | | | |
|---|---|---|---|
| 9,880,805 B1* | 1/2018 | Guralnick | G06F 3/165 |
| 11,157,087 B1* | 10/2021 | Ching | G06N 3/045 |
| 11,161,011 B2* | 11/2021 | Neumann | A63B 24/0062 |
| 11,173,341 B2* | 11/2021 | Kim | A63B 24/0006 |
| 11,195,152 B2* | 12/2021 | Gallagher | G06Q 10/1093 |
| 11,439,870 B2* | 9/2022 | Werner | G06Q 10/06315 |
| 11,488,701 B2* | 11/2022 | Bettencourt Da Silva | |
| | | | G06N 20/00 |
| 2015/0004578 A1* | 1/2015 | Gilley | G16H 10/20 |
| | | | 434/236 |
| 2015/0185967 A1* | 7/2015 | Ly | G06F 3/0488 |
| | | | 715/720 |
| 2016/0151674 A1* | 6/2016 | Rauhala | G06Q 30/0269 |
| | | | 434/247 |
| 2017/0039480 A1* | 2/2017 | Bitran | G16H 40/63 |
| 2017/0259119 A1* | 9/2017 | Hoffman | G16H 20/30 |
| 2018/0071583 A1* | 3/2018 | Paiz | A63B 24/0062 |
| 2019/0205839 A1* | 7/2019 | Dotan-Cohen | |
| | | | G06Q 10/063116 |
| 2021/0379447 A1* | 12/2021 | Lee | A61B 5/11 |
| 2022/0062707 A1* | 3/2022 | Bedekar | G16H 20/30 |
| 2022/0176065 A1* | 6/2022 | Youngblood | A61B 5/486 |
| 2022/0273269 A1* | 9/2022 | Capodilupo | A61B 5/4812 |

* cited by examiner

*Primary Examiner* — David Phantana-angkool
(74) *Attorney, Agent, or Firm* — Lowenstein Sandler LLP

(57) ABSTRACT

A system and method for providing recommendations for a workout by a user. The system includes a workout engine configured to select the workout for the user based on user input and/or historical data, and one or more data sources, each of the one or more data sources providing information associated with the user and/or the workout. The system further includes a recommendation engine configured to receive the information associated with the user and/or the workout from the one or more data sources, and to generate one or more recommendations about the workout and/or the user before, during and/or after the workout by the user, the one or more recommendations being configured to optimize the performance of the workout by the user.

10 Claims, No Drawings

WORKOUT RECOMMENDATION ENGINE

TECHNICAL FIELD

The subject matter described herein relates to methods and apparatuses for improving a workout by a user, and more particularly to a workout recommendation engine.

BACKGROUND

Various systems and software applications exist for suggesting a workout for a user, in order to meet the user's fitness or health goals. However, conventional workout generation or suggestion systems and software are not able, nor configured, to dynamically adjust current or future workouts for a user.

What is needed is a recommendation engine and workout engine for adjusting current and future workouts.

SUMMARY

In one aspect, a system and method includes a recommendation engine (RE) and a workout engine (WE), each being configured for monitoring, tracking and evaluating a user's performance of a workout, and for adjusting current and future workouts. The workout can be adjusted based on real-time feedback, and the recommendation engine will take into account the adjustments and results on the user, as further described herein.

In one aspect, a system for providing recommendations for a workout by a user is described. The system includes a workout engine configured to select the workout for the user based on user input and/or historical data, and one or more data sources, each of the one or more data sources providing information associated with the user and/or the workout. The system further includes a recommendation engine configured to receive the information associated with the user and/or the workout from the one or more data sources, and to generate one or more recommendations about the workout and/or the user before, during and/or after the workout by the user, the one or more recommendations being configured to optimize the performance of the workout by the user.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The drawings, which are incorporated by reference herein, and constitute a part of this specification, show certain aspects of the subject matter disclosed herein and, together with the description, help explain some of the principles associated with the disclosed implementations.

When practical, similar reference numbers denote similar structures, features, or elements.

DETAILED DESCRIPTION

This document describes a Recommendation Engine (RE) and Workout Engine (WE) for adjusting current and future workouts. Such workouts are described in: U.S. Non-Provisional application Ser. No. 15/017,477, filed Dec. 27, 2011, entitled "FITNESS AND WELLNESS SYSTEM WITH DYNAMICALLY ADJUSTING GUIDANCE"; U.S. Non-Provisional application Ser. No. 13/720,936, filed Dec. 19, 2012, entitled "FITNESS AND WELLNESS SYSTEM WITH DYNAMICALLY ADJUSTING GUIDANCE"; U.S. Non-Provisional application Ser. No. 15/017,537, filed Feb. 5, 2016, entitled "PHYSICAL ACTIVITY COACHING PLATFORM WITH DYNAMICALLY CHANGING WORKOUT CONTENT"; and U.S. Non-Provisional application Ser. No. 14/251,457, filed Apr. 11, 2014,entitled "PHYSICAL ACTIVITY COACHING PLATFORM WITH DYNAMICALLY CHANGING WORKOUT CONTENT", the contents of all of which are incorporated by reference herein for all purposes.

In some implementations, the RE can adjust a workout based on real-time feedback, the recommendation engine will take into account the adjustments and results on the user. The RE can also calculate user's possible travel and changes in different time zones. In the mobile phone logic, the time zone is automatically adjusted when the user arrives in different time zones. The recommendation engine can record and calculate the 'lost' time and 'gained' time between time zones. Further, the RE can monitor the duration of travel time (i.e. time, when the mobile phone's time is not being updated, or the phone has been at least partially inactive, such as in airplane mode).

If the user is traveling extensively or losing time due to travel, the RE can suggest an easier workout for the next workout. Also, certain audio prompts can be included into the next workout, acknowledging that the user has travelled and would therefore need to have an easier workout due to jetlag.

During the workout, the Workout Engine (WE) can also compare normal statistics from history versus current statistics, and make voice announcements of the difference in performance. Further, when measured results are lacking in effort (i.e. lower pace, lower HR, lower power vs normal or average workout), the RE can change the user's music to more uplifting, up-tempo music to energize the user. Accordingly, the WE includes a memory to store data about the user's music, such as tempo or other tonal qualities.

The RE can be configured to monitor music and performance during workouts, and builds a correlation of HR/pace (effort) and the played music tempo (beats per minute).

Therefore, the RE can know what type/tempo music will energize the user to increase or decrease the effort.

In addition of the user time zone traveling, the RE can be reading a user's mobile phone calendar. Based on the amount/times of meetings and number of meetings vs free time (non-allocated time on calendar), the RE can adjust user's workout durations and schedule. It is assumed that user's meeting and work load is accounting for 'mental' stress which can also affect user's ability for physical stress.

As the user engages in a workout, the RE can also add an extra period at the end of the workout routine, or this can be measure continuously after the workout, to determine the user's recovery speed, such as time for the user's HR returning to normal. The RE can also monitor user behavior and functions, such as sleep quality and durations, or nutritional intake, for instance, to determine recovery times and readiness for a particular workout.

When the RE has determined the workout and WE is starting the workout, a user can have a dialogue with an AI coach with natural language processing capabilities to adjust the workout with conversational prompts, such as using artificial intelligence (AI) modules to execute an exemplary conversation such as: "How do you feel today?" User: "I'm feeling tired". AI coach "OK, let me adjust your workout to be easier."

In some implementations, the RE can be configured to determine user's likes and hobbies based on Facebook® and other social media data. RE can read user's actions in the mobile phone and categorize the user into a group of users, such as, for example, whether the user likes 'football' as the user is following NFL news. As user is put into a specific group, the WE may select prompts from the prompt library that are relevant to i.e. the hobby of the user. This might include news and audio clips of the NFL teams, results, etc. Also, the voice for the coach maybe selected to be a football coach.

The RE can also use sensor information from wearable garments or devices, such as shirts or shorts with built-in sensors, such as accelerometers, pressure sensors, and the like. Based on the activity and movement data of these sensors, the RE can determine muscle groups that have been used and their physical load, and then recommend workouts that include muscle groups that are most ready for training.

The RE can also work with meal plans and adjust meal plans. If a user is not able to complete a workout as planned, the RE may adjust the user's meal plan and i.e. recommend a meal with less calories to maintain the calorie goals for the day/week. In some implementations, a system can follow a user by a drone and video record the running form of the user, where the user is wearing Augumented Reality (AR) eyewear, such as glasses, and able to see his/her own running form and therefore focus on correcting the running form based on the coaching. In still other implementations, a system uses a user's genetic information or recommending workouts.

In some implementations, a method is provided to certify a user's movements are authentic and not fake. When the user performs a workout, certain accelerometer movements are recorded by a phone or a wearable device. Over time, the system can build an 'image' of the user's movements. The measurements include such as force of impact when walking/running to determine user's weight, heart rate patterns, etc. that are all carry individual aspects of the user. This image or a 'fingerprint' is used to compare new movements and therefore the RE can validate the user's movements to be by the certain user and authentic. The authentication is important when user is compensated or gets a reduced rate i.e. insurance cost, based on activity levels of the user.

To combat errors in heart rate monitor (HRM) Readings, an improved HRM with an audio circuit can be provided. Electrocardiogram (EKG) is done via induction of electric signals. Sometimes connectivity and other electronic interference affects the readings. The system can include an audio microphone on the HRM to act as a heart rate detection circuit. A microphone can also be used to estimate breathing rate.

In some implementations, a wearable recorder is provided for conversational artificial intelligence (AI), using an AI module. The system can include a personal assistant for conversational AI (records audio and sends to Amazon Alexa or Google Assistant/Cortana later). The AI module can detect certain audio phrases that trigger recording. Recorded messages are sent when a device is connected with the Internet, such as when a WIFI router or other wireless transmission medium is in reach.

The system can further include an audio recorder to listen to user during activity and adjustable workouts based on audio recordings. The user may be engaging in a workout that requires certain intensity. As the user is engaged in the activity, a microphone is recording the surrounding sounds to detect user movements and intensity. The microphone maybe trained to look for breathing sounds and frequencies to try to determine user's breathing rate. Similarly, the microphone can be there to detect sounds of weight hitting the floor, or the user's movements just as jumps. Even minor sounds can be correlated with the move to assist i.e. in counting the reps the user is doing. The microphone can be part of a smart phone or a remote circuit that connects with the smartphone or computer.

In still other implementations, a system can include use of a headset microphone and/or electrical cord harmonics to estimate user movements. During an activity, normal headphones have a cord that moves with the user. During the activity, the headset microphone can be active and listening.

While workout audio is being played during a workout, the RE can encourage user performance to reach new thresholds or certain new goals (i.e. comparing a current performance with a previous record and calculating the difference, and when the difference is small, the RE can inject a prompt). The goals can be personal records, or other results that might motivate the user, such as rewards or discounts on health insurance.

During a race or an event, the RE can be preconfigured to analyze the course elevations, and calculate and coach the user for optimal performance to distribute efforts to a best event time or pacing. The RE can further generate topographical guidance, such as tips about how to navigate certain topographical features. The RE can analyze surrounding topographical area and guide the user to an area suitable for the specific workout, such as, for example, guiding the user to an appropriate hill for a hill-repeat workout. Topographical and/or terrain information can be obtained from Global Positioning System (GPS) Data, a mapping service, a navigational software application, or the like, or any combination thereof.

The RE can be configured to analyze users running form and performance (pace, stride length, stride frequency), and based on a user's athletic performance, recommend suitable apparel, shoes, nutrition plans, that are optimized/designed for the user's athletic level. Accordingly, the WE and RE can be associated with a database or other memory storing data about such suitable workout-related items. Third party retailers, brands, vendors, product suppliers, or the like, associated with the aforementioned apparel or products, can interface with the database or other memory, or directly with the RE, via an application programming interface (API), that can be configured to receive the data for product placement and/or recommendation.

In some implementations, the RE can be configured to acquire knowledge about gym equipment within a gym location, and adjust workout based on available machines. The RE can acquire the knowledge via Near Field Communication (NFC) from the equipment, or the gym equipment manifest can be downloaded from a website or other site on the Internet. Further still, a gym can interface with the RE or a database associated with the RE via an API.

In yet other implementations, the RE can be configured to acquire user performance data and user profile data, and correlate the performance data with predicting over-use or injury to the user. By collecting vast amount of user data and using machine learning, the RE can learn to predict injury and adjust the workout for the user and/or recommend physical therapy or other fitness treatments to reduce the risk of injury. In some implementations, the RE can be associated with one or more therapy or treatment service providers over a network or via an API, so as to leverage these provider's knowledge base.

In yet other implementations, the RE can be configured to schedule users' workouts based on genetic markers. For example, certain genetic markers can suggest that a specific user is most efficient to work out in the morning or during the evening. This feature of the RE can also rely on historical data, such as user historical data or historical performance data, which can be correlated to the genetic data or markers.

Over time and after a number of workouts, the RE can detect a user's performance and/or reactions with different coaching voices/coaching styles, and recommend a workout with a pre-recorded or computer-generated instructor/coach that will result in the most effective performance. For example, the RE can be configured to match a coach and voice tone that is best drives performance.

In some implementations, the RE can provide a nutritional recommendation for fitness performance. For example, the RE can recommend one or more meals or beverages, and a time for consumption. The time can be a specific time, or can be a time window. The time can be associated with a time a workout is recommended, based on a specific user and their user profile. For instance, some users may have a better and more efficient workout in the morning, while other users might benefit from an evening workout. In some further implementations, the RE can be configured to dynamically adjust the recommendation based on prior performance. For instance, using statistical probability calculations, the RE can limit the recommended performance level that is feasible, such as within a number of standard deviations from the statistical norm, for a user based on their performance history, a cohort's performance history, and success level of either of prior recommendations.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method comprising:
   selecting, by a processing device, a workout for a user based on one or more of a user input or historical data associated with the user;
   generating, based on historical data, an image corresponding to a set of movements of the user;
   receiving, from one or more data sources, information associated with one or more of the user or the workout;
   receiving, from a mobile device of the user, information relating to a calendar of the user;
   setting, based on the information relating to the calendar, an adjusted duration of the workout;
   measuring, via a sensor, performance data of the user relating to the workout having the adjusted duration;
   identifying a movement of the user from the performance data;
   authenticating the movement of the user by comparing at least a portion of the performance data to at least a portion of the set of movements of the image associated with the user;
   generating, at least one of before, during, or after the workout, one or more recommendations associated with one or more of the workout or the user, the one or more recommendations being configured to adjust performance data associated with the workout; and
   displaying the one or more recommendations associated with the one or more of the workout or the user.

2. The method of claim 1, wherein the information associated with one or more of the user or the workout provided by the one or more data sources comprises topographical information about a geographical environment of the workout.

3. The method of claim 1, wherein the information associated with one or more of the user or the workout provided by the one or more data sources comprises at least one of genetic information of the user or one or more genetic markers of the user.

4. The method of claim 1, further comprising:
   selecting, based on the performance data, an audio file comprising audio associated with the workout; and
   generating, by an audio processor, the audio associated with the workout.

5. The method of claim 1, further comprising recording, by a microphone, one or more sounds produced by the user during the workout.

6. The method of claim 1, further comprising generating the workout for the user based at least on one or more selected portions of one or more workouts.

7. The method of claim 1, wherein the workout comprises a meal plan for the user.

8. The method of claim 1, further comprising collecting, via one or more additional sensors, sensor data associated with the user.

9. The method of claim 8, wherein the one or more additional sensors are formed in a wearable garment configured for being worn by the user during the workout.

10. The method of claim 8, wherein the one or more additional sensors comprise at least one accelerometer.

* * * * *